United States Patent
Von Behren et al.

(10) Patent No.: US 6,558,324 B1
(45) Date of Patent: May 6, 2003

(54) SYSTEM AND METHOD FOR STRAIN IMAGE DISPLAY

(75) Inventors: Patrick L. Von Behren, Bellevue, WA (US); Dong-Cyuan Liu, Mercer Island, WA (US); Jian-Feng Chen, Issaquah, WA (US)

(73) Assignee: Siemens Medical Solutions, Inc., USA, Malvern, PA (US)

( * ) Notice: Subject to any disclaimer, the term of this patent is extended or adjusted under 35 U.S.C. 154(b) by 0 days.

(21) Appl. No.: 09/994,589

(22) Filed: Nov. 20, 2001

Related U.S. Application Data

(60) Provisional application No. 60/252,934, filed on Nov. 22, 2000.

(51) Int. Cl.$^7$ .................................................. A61B 8/00
(52) U.S. Cl. .................... 600/440; 600/437; 600/441; 600/443
(58) Field of Search ............................. 600/437–472

(56) References Cited

U.S. PATENT DOCUMENTS

| | | | | |
|---|---|---|---|---|
| 5,178,147 A | * | 1/1993 | Ophir et al. ................. | 600/437 |
| 5,538,004 A | * | 7/1996 | Bamber ....................... | 600/443 |
| 5,873,830 A | * | 2/1999 | Hossack et al. ............. | 600/447 |
| 5,919,139 A | * | 7/1999 | Lin .............................. | 600/443 |
| 5,961,460 A | * | 10/1999 | Guracar et al. ............. | 600/440 |

\* cited by examiner

*Primary Examiner*—Francis J. Jaworski
*Assistant Examiner*—William C. Jung

(57) ABSTRACT

A region of interest (ROI) of a patient's body is repeatedly scanned using an ultrasound transducer array. Data sets representing an image property, such as intensity, from portions of the ROI are used to calculate a representation of the displacement profile within the ROI at different stress levels. From the displacement profile, a function of strain is also preferably calculated. According to one aspect of the invention, a data set representing an estimate of the elasticity profile within the ROI is color-coded and is displayed along with a B-mode display in a single, overlaid display. According to another aspect of the preferred embodiment of the invention, the display of elasticity is adaptively persisted as a function of, for example, a measure of image quality. The invention also provides an on-screen guide that indicates to a user a measure of quality of each of a series of estimated displacement data sets.

32 Claims, 5 Drawing Sheets r(i,j,k)    r(i,j,k+1)

E(i,j,k)

SYSTEM AND METHOD FOR STRAIN IMAGE DISPLAY

CROSS-REFERENCE TO RELATED APPLICATIONS

This application claims priority of now abandoned U.S. Provisional Patent Application No. 60/252,934, filed Nov. 22, 2000.

BACKGROUND OF THE INVENTION

1. Field of the Invention

This invention relates to diagnostic ultrasonic imaging in general and in particular to the display of ultrasonic imaging data relating to the elastic properties of scanned tissue.

2. Description of the Related Art

Ultrasonic elasticity imaging is a technique whose use has become more widespread as the processing power of ultrasonic imaging systems has grown enough to handle the often heavy computational loads required by the technique. As is well known, elasticity imaging is based on the same principle as the manual palpation that has been used by physicians for millennia: Tumors and other "lumps" can often be detected simply by compressing the surrounding tissue. Even to this day, for example, most breast cancers are discovered by self-examination using manual palpation, and physicians still rely on palpation to detect potential tumors of the liver and prostate.

The principle of manual palpation is well known and is based on the property that if a compressive force is applied to an elastic body, then it will deform. If a relatively stiffer, that is, less elastic, inclusion is located within a region of the body, then a constant compressive displacement will deform the region above the stiff object more than the adjacent regions. Because tissues are elastic, the more they are deformed, the greater counter force they generate; in other words, large stress leads to large deformation. If a diagnostician applies the pressure with her fingers, then she will often be able to feel the stress distribution above the palpated region. To sum up the procedure, if one presses on body tissue, then one can often feel "lumps."

Ultrasonic elasticity imaging emulates manual palpation, but has several advantages. One advantage is that it can provide information about tissue elasticity as deep as the ultrasound can penetrate, which is usually deeper than a physician can feel with her fingers. Another advantage is that ultrasonic elasticity imaging has relatively high sensitivity, although resolution and sensitivity are reduced for deeper inclusions. Yet another advantage is that ultrasonic elasticity imaging can provide a 2-D cross sectional view of the elastic properties of the object. Still another advantage is that information about tissue elasticity obtained using ultrasound can be more easily quantified, and can be stored for later analysis.

Using ultrasound to create an image of the displacement or strain profile (which is related to elasticity) within a region of insonification often reveals structures that are invisible or hard-to-detect in a conventional B-mode image either because of noise, or because the acoustic impedance of the internal structure is not different enough from the surrounding tissue to provide adequate B-mode contrast. In many cases, however, the elastic properties of such structures are so different from those of the surrounding tissue that an image of the strain profile will show the structure clearly, or at least much more clearly than a B-mode image.

Because strain is a function of the derivative of displacement, at least two B-mode images are required for each estimate of strain. Accordingly, in ultrasound elasticity imaging, two B-mode frames are generated while the clinician uses the ultrasound transducer (or, in some cases, an external mechanism) to vary the stress on the imaged portion of the patient's body, for example, through cyclical compression and decompression. The 2-D displacement function is then estimated by comparing the scans at different stress levels. Object strain and/or elastic constants can then be estimated from the estimated displacement function.

Many different methods have been proposed to create an estimate of strain within a 2-D scan region once two B-mode frames are available for comparison and analysis. The algorithms underlying these known methods typically rely on cross-correlation, echo data modeling, block matching, direct strain estimation using adaptive local stretching algorithm, and the analysis of a deformable model. Once an ultrasound system generates information about the strain distribution within the scanned portion of the patient's body, it must be displayed in some way. The conventional way to display elasticity data is by converting the strain values to corresponding gray-scale values and then to present these in the same way as any B-mode image.

Even the most accurate algorithm for estimating a strain profile within a region of a patient's body is all but useless, however, if the data are not presented to a physician in such a way that he can clearly see the inclusions the scan detected. Because elasticity imaging is essentially a function of a difference between B-mode images, equivalent to a first derivative of local (often, pixel-to-pixel) displacement, it is particularly sensitive to noise. Moreover, several cycles of compression and relaxation are usually gone through during the course of a typical elasticity scan. At each time of transition, or whenever else the physician stops changing the degree of compression, there will be little or no change in displacement between temporally adjacent B-mode frames. At these times, most of what the physician will see on the display will be either noise or artifact. This can be very distracting, and may even prevent the user from making sense of the display when it is showing valuable elasticity information.

The distractions caused by noise and artifacts are even more pronounced in the typical gray-scale displays of elasticity data. Gray-scale images may be clear enough in conventional B-mode imaging, in which one tries to hold the transducer relatively still once a structure of interest has been acquired, but elasticity imaging typically requires the user to cyclically press and release the probe against the patient's body. Consequently, elasticity displays are by definition dynamic, with many frames of "noise" at transitions between compression and decompression.

One way to avoid this is for the various frames of elasticity data to be stored either digitally, on tape, or on some other recording medium, for later display in a "cine" mode. Even then, however, the user must decide which frames are showing diagnostically useful information and which should be ignored.

What is needed is therefore an improved display of elasticity data. Ideally, the display system should also make it easier for the user to identify and concentrate on display frames that have a relatively high signal-to-noise ratio. This invention provides such a display.

SUMMARY OF THE INVENTION

The invention provides an ultrasonic imaging method and system implementation that have various aspects. Common to all embodiments of the invention is that a region of interest (ROI) of a body is scanned a plurality of times using an ultrasound transducer in order to acquire a first and second set of intensity values. Each intensity value in each set represents an imaging property of a respective portion of the ROI, such as echo signal strength.

According to one aspect of the preferred embodiment of the invention, a gray-scale (B-mode) representation of the first set of intensity values is generated in the conventional manner. A set of elasticity values—an elasticity data set—is also calculated as a function of differences (corresponding, for example, to displacement) between corresponding intensity values in the first and second sets of intensity values. A color representation of the elasticity data set is then also generated by color-coding the elasticity values. Both the gray-scale (B-mode) and color (elasticity) representations are then displayed simultaneously as a single, registered, overlaid display.

The overlaid display is preferably generated as a linear combination of the gray-scale representation and the color representation, for example, with the visibility of the gray-scale and color representations, respectively, being functions of a transmission coefficient. The transmission coefficient may be fixed, set automatically, or made user-adjustable. The overlay may also be generated as a non-linear combination, for example, the product, of the two representations.

According to another aspect of the preferred embodiment of the invention, the display of the elasticity data set is adaptively persisted. The degree of persistence applied to a current elasticity display is preferably dependent either on a quality factor indicating the quality the current elasticity frame, or on one or more previous elasticity frames, or on both.

According to yet another aspect of the preferred embodiment of the invention, a measure of quality of each of a series of displayed frames is calculated. A graphical representation of this quality measure is then preferably displayed along with the current frame. By either maneuvering a displayed marker or by stepping through display frames (as in conventional cine), the user can select a particular frame for display, for example, a frame with high indicated quality, guided by the displayed graphical representation of the quality measures for the different frames.

DETAILED DESCRIPTION

This invention relates in general to a system and a method for generating a display of the elastic properties of a portion of a body scanned with ultrasound. It is particularly useful for detecting the noisy strain frames during the transition between the compression and decompression process. It also provides for calculation of factors that indicate at least approximately which strain frames have, or are most likely to have, a high signal-to-noise ratio (SNR).

The invention also provides for detection of local motion so as to allow for compensation of the motion of the probe. This in turn makes it possible for the system to increase the SNR in the display of elasticity by providing proper spatial registration. A persistence technique is preferably also applied to reduce distraction caused by low-quality displays of elasticity in regions of transition between compression and decompression. In the preferred embodiment of the invention, by suppressing detected noisy strain frames, the system is able to display the original tissue image with a color-coded, transparent, strain image overlaid onto (or instead of) a conventional gray-scale image in order to indicate the spatial information of the strain image.

The invention also provides an optional interactive graphics tool that helps the user see how best to maneuver the probe and which portions of recorded strain data most accurately reflect the elastic properties of the imaged tissue. These features are explained below individually. First, though, the main hardware and software components of a system according to the invention are described.

Main System Components

Figure 1:
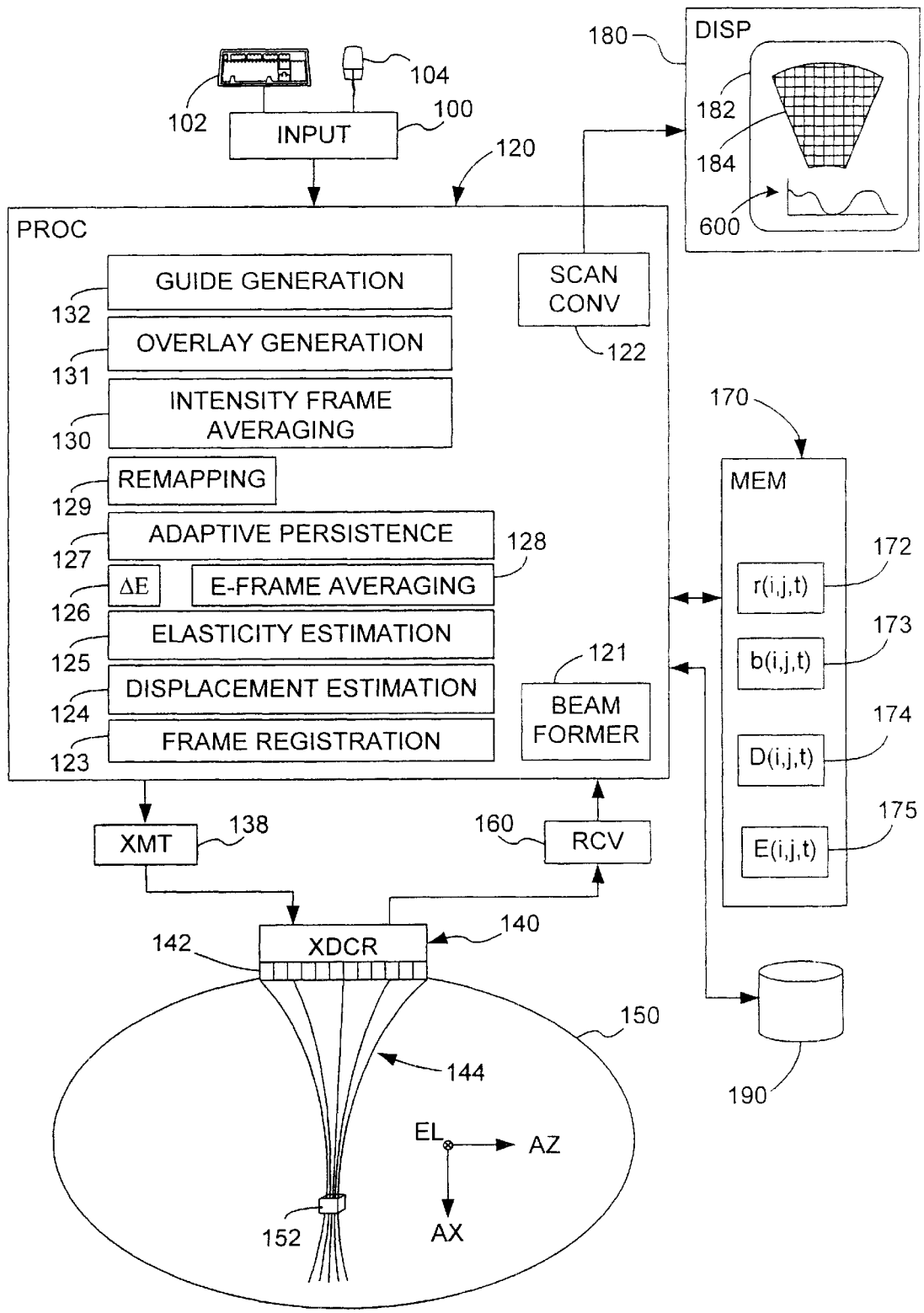
FIG. 1 is a block diagram that illustrates the main components of an ultrasonic imaging system that is suitable for implementing the invention.

FIG. 1 illustrates the main components of an ultrasonic imaging system that is suitable for implementing the invention. The user enters various conventional scan parameters into an input unit 100, which typically comprises conventional hardware input ports and any necessary drivers within an operating system and which typically includes such devices as a keyboard 102, knobs, a mouse (or trackball, or joystick, etc.) 104, and/or buttons. The input unit is connected to a processing system 120, which will typically be an electrically connected and cooperating group of processors such as microprocessors and digital signal processors; the processing system may, however, also be implemented by a single processor as long as it is fast enough to handle the various tasks described below.

As in known systems, the processing system 120 sets, adjusts, and monitors the operating parameters of a conventional transmission control circuit 138. This control circuit 138 generates and applies electrical control and driving signals to an ultrasonic probe, that is, transducer 140, which includes an array 142 of piezoelectric, capacitive, or similar elements. As is well known in the art, the elements generate ultrasonic waves when electrical signals of the proper frequency are applied to them.

By placing the probe 140 against the body 150 of a patient, these ultrasonic waves enter a portion (an "interrogation region," or a "region of interest") of the patient's body. By varying the phasing, amplitude, and timing of the driving signals in a conventional manner, the ultrasonic waves from the respective array elements are formed into a transmit beam 144. The beam typically converges at a focal depth, beyond which it once again diverges. The transmit beam is steered in the azimuth/lateral direction AZ and the elevation direction EL, and is focused in the depth/axial direction AX so as to concentrate the ultrasonic energy of the beam onto a volume of focus 152 within the interrogation region. The volume 152 corresponds to one measurement point or sample, even in the case of 2-D imaging. In FIG. 1, for example, the beam 144 is shown as being steered just left of the array centerline, that is, the line that would extend from the center of the array and perpendicular to it.

In the description of the invention below, it is assumed that the ultrasound scan produces 2-D sets of data samples, that is, scanning is done in a plane. As those skilled in the art of designing ultrasound imaging systems will appreciate, however, the invention may also be used in implementations where entire 3-D interrogation regions are imaged either as a whole or through compilation of imaging data from different scan planes. In this case, any known projection algorithm may be used to select a 2-D subset for processing and display using the techniques according to the invention.

Without loss of generality, and for ease of illustration, it is assumed that each data set is acquired in the axial-azimuthal plane, where the axial (AX) dimension corresponds to the return of an acoustic wave front along a beam line, whereas the azimuthal direction (AZ) is a spatial dimension perpendicular to the axial direction and over different breadlines.

When any point, such as point 152, in the interrogation region is insonified, the transducer is typically switched from the transmit mode to a receive mode. In the receive mode, ultrasonic energy from the waves created by the elements 142 is reflected back (back-scattered) as a return echo signal to the array. The elements 142 in the array 140 then convert the small mechanical vibrations caused by the echo signal into corresponding radio-frequency (rf) electrical signals. Amplification and other conventional signal conditioning are then applied to the return signals by a reception controller 160. This processing typically includes, as needed, such known signal conditioning as time-gating, gain compensation, and diffraction compensation, in order to identify the echo signals that correspond to each scanned element in the interrogation region. The type of conventional signal processing needed will in general depend on the particular implementation of the invention and can be chosen using known design methods.

The reception controller 160, all or part of which is normally integrated into the processing system 120 itself, converts the ultrasonic, radio-frequency (rf) return signals (typically on the order of a few to tens of megahertz) into lower frequency ranges for processing, and may also include analog-o-digital conversion circuitry. This is well known in the art of ultrasonic imaging. If not included in the reception controller 160 itself, the processing system 120 will also usually include a beamformer 121 that converts the conditioned return signals into corresponding return beams, each of which normally corresponds to the echo from a transmit beam.

In conventional B-mode scanning, each point, that is, sample, within the interrogation region can then be represented as an intensity (brightness) value. The entire interrogation region can therefore be represented as a discretized pattern (matrix) of brightness or signal intensity values, which are stored as frame data in a memory 170.

The interrogation region is normally not in the same shape as what the user wants to see displayed. Even when it is, the digital acoustic intensity values that make up the frame data are normally not in a form suitable for driving a conventional gray-tone or color display directly. The acoustic intensity values for a selected 2-D sub-set (scan plane) are therefore applied to a conventional scan converter 122, which converts the digital acoustic values into display intensity values that are suitable for use in driving a display device 180.

The display device 180 typically includes or is connected to a conventional display driver and includes a screen 182 (for example, LED or CRT) that is divided into an x-y (or polar) matrix or pattern 184 of picture elements or "pixels" that make up an image that the user can view and interpret. Note that a displayed image element will often be made up of more than one pixel, but that this will depend on the relative resolutions of the scan and of the display. The invention does not require any particular relative resolution.

An entire displayable 2-D matrix of intensity values cannot normally be acquired using a single transmit pulse; rather, the brightness for each point in the interrogation region is scanned and converted separately. Nonetheless, scanning is typically fast enough that the brightness values determined for all the points in a given image frame can be considered to have been acquired simultaneously.

For any given scan plane, the invention stores intensity values for the interrogated points that lie in the plane. Actual acquired data is often from a trapezoidal or "fan-shaped" interrogation region and is then scan-converted into whatever shape is preferred for the actual display. It is assumed here, merely for the sake of illustration and ease of understanding that each set of frame data can be represented as an m-by-n matrix of intensity values for points (positions) located i axial distance units in the axial/depth direction and j lateral distance units in the lateral/azimuthal (j) direction. In general, the scan points along any given A-line (in the axial direction) are at least approximately equally spaced, and adjacent A-lines (in the lateral direction) are also approximately equally spaced from any predetermined origin. If this assumption is not accurate in any given application of the invention, then conventional scaling and indexing routines may be used to represent the scan data for purposes of the calculations described below.

Frame data is stored in a memory portion 172 as intensity values $r(i,j,k)$. Here, the index k refers to the frame number; thus, frame k+1 is the frame acquired one scan period after frame k. The time difference between acquisition of frame k and frame k+1 will be the inverse of the frame rate, which is known for any given transducer and scan. The number of frames stored will depend on the amount of memory available and the needs of the particular implementation. If the system includes mass storage 190 such as a tape, writeable CD-ROM or high-capacity disk, then enough frames may be stored in such a device in order to allow for a conventional "cine" (from "cinematographic") display mode suitable for viewing and analysis (or transmission) at any time, even after the imaging session is completed. The various data structures shown as being stored with the memory 170 may therefore also, or instead, be stored in the mass storage device 190. All that is required to use the simplest embodiments of the invention is two consecutive sets of frame data.

The intensity values $r(i,j,k)$ stored are preferably measures of the intensity of the radio-frequency (rf) return signals from each of the elements at location (i,j) in the interrogation region at different levels of stress—the rf data will typically yield the most accurate estimates of strain. The invention may also operate, however, directly on the brightness values $b(i,j,k)$ that are derived in any known manner from the rf data for use in a conventional B-mode display. Merely for the sake of simplicity, the term "B-mode" is used below collectively to indicate the mode in which the intensity values are stored. Both the rf data for several frames and at least the brightness data for a current visible display are preferably stored in respective memory portions 172, 173.

The invention includes several software modules (in particular, modules 123–131) that implement the various procedures that are carried out in different embodiments of the invention. These modules will be described below in conjunction with the description of their respective operations, which are also illustrated by the procedural block diagram shown in FIG. 3. All of these software modules may be implemented using known programming techniques with conventional hardware support as needed in order to provide necessary calculation speed.

Stress Generation

Strain is, of course, a result of stress. The cause of the strain in elasticity imaging in the preferred embodiment of the invention is the non-constant force of the ultrasound transducer that the user (sonographer or physician) presses against the patient's body during the examination. The main advantage of allowing the user (diagnostician) to generate the force by pressing the transducer against the patient's body is that this allows the user to easily vary the pressure and see the imaged results. Any other conventional device may be used, however, to apply pressure to the surface of the scanned body region; indeed, depending on what portion of the patient's body is to be imaged, the body itself may exert a sufficient time-varying force on the interrogation region, even from within.

The general method followed in elasticity imaging is as follows: By pressing an ultrasound transducer against a portion of a patient's body, the tissue within the interrogation region is compressed. Note that, in the context of this invention, "compression" may also be negative, which of course implies expansion from a compressed state. Expansion will occur, for example, when the user presses the transducer less firmly against the patient: In the normal course of a strain-image scan, the user will apply pressure cyclically because imaging of strain relies on changes in compression, which lead to displacement (and thus strain) of acoustically reflective structures within the interrogation region.

The cyclical compression and decompression of the interrogation region is the cause of much noise and distraction using prior art display methods for elasticity data. Recall that calculations of displacement are usually based on functions of the frame-to-frame change, that is, the time derivative of intensity of local regions of the frames, which is equivalent to a calculation of the local velocity of portions of the interrogation region. Because a sequence of strain images always represents a compression or decompression cycle in the exam, the calculated strain values at the transition frames, where frame-to-frame displacement is relatively small, in general are not reliable and result in errors that appear as artifacts in the display. These artifacts are often a significant distraction, and reduce the diagnostician's ability to interpret the displayed strain information in either real-time or a cine loop. The various embodiments of this invention help reduce this distraction.

Frame Registration

Estimations of tissue elasticity rely on estimations of local displacement, that is, movement, of the tissue. Once the region of interest is scanned and represented as the frame $r(i,j,k)$ of intensity values, in order to determine the movement of a region of tissue, it is necessary to know which element in a subsequent frame corresponds to a given element in a current frame. Before a displacement and elasticity profile can be calculated, the intensity frames $r(i,j,k)$ should be registered, that is, translated such that each pixel in subsequent frames spatially matches, as closely as possible, and preferably exactly, the pixel corresponding to the same tissue portion in a reference frame (for example, the first imaged frame, or the first in a sequence of high-quality frames, or simply the first of a pair of intensity frames). The processing system therefore includes a module 123 that performs the frame registration. In other words, the value $r(i,j,k)$ for the position $(i,k)$ should correspond as closely as possible to the same tissue portion as the value $r(i,j,k+1)$ in the following (or preceding) intensity frame. The processing system therefore includes a module 123 that performs the frame registration.

Any known registration algorithm may be used to register the intensity frames. In one prototype of the invention, the preferred image registration procedure was based on a minimum-sum-absolute-difference (MSAD) motion estimation method to calculate local tissue motion during the compression/decompression period. According to this method, the image frame data in each intensity frame $r(i,j,k)$ is divided into windows, for example, of SxS elements (such as pixels) each, where S is determined by conventional experimental methods. (Of course, the windows could also be rectangular, or have some other shape.) For each current window in frame k, the subsequent (or previous) frame $r(i,j,k+1)$ is then searched for the SxS pixel window for which the sum-absolute-difference (or some other metric, such as least squares) in intensity values as compared with the current window is a minimum. The components of spatial difference between the matching frames then form a local motion vector. The local motion vector in turn gives an estimate of the "best" shift of the elements in the subsequent frame that brings them into registration with the corresponding elements in the previous frame.

Subsequent computations of displacement can then be performed window-by-window. Alternatively, a single, global motion vector may be used to register all frame elements, for example, by accumulating the local motion vectors of the different windows starting from a reference frame and then averaging the local vectors.

Displacement Estimation

This invention does not relate directly to how an estimate of strain or elasticity is generated, but rather to how the strain or elasticity data, once obtained, is processed and displayed. Nonetheless, the invention does assume that some technique is implemented within the system in order to generate elasticity data based on the return signals, or that the elasticity data is made available in some other manner, for example, via a network or on a mass storage medium.

Estimations of tissue elasticity usually rely on estimations of local displacement of the tissue. In other words, the system compares two (or more) consecutive frames of intensity (or, equivalently, strain) data $r(i,j,k)$ and $r(i,j,k+1)$, which are assumed to have been registered as described above, in order to determine how far a particular portion of the tissue has moved from one frame to the next. Expressed differently, the system calculates an array $D(i,j,k)$ of displacement values (shown in FIG. 1 as being stored in memory portion 174) as $D(i,j,k)=r(i,j,k)\hat{x} \, r(i,j,k+1)$, where $\hat{x}$ is the operator that characterizes the chosen displacement estimation algorithm.

There are many different known methods for determining the displacement profile within an ultrasound interrogation region. Suitable algorithms include those that rely on cross-correlation, echo data modeling, block matching, direct strain estimation using an adaptive local stretching algorithm, and the analysis of a deformable model (for example, a deformable "mesh"). Using block matching, for example, a search algorithm attempts to match or register a window of pixels (a subset of $r(i,j,k)$) chosen around each of a number (including all) of the scanned data points in one frame with a window of equal size in the subsequent data frame. When the "best" match is found in some predefined sense, then the linear offset in the two windows is taken to be the displacement of the given central pixel.

The "best" fit may be defined in many different ways. For example, the search routine may look for the window in the subsequent frame that is most highly correlated with the base window. Correlation is often based on speckle within the respective frames. As just one example of an alternative, the "best" fit between the windows is taken to be when a cost function is minimized. This cost function C generally takes the form: $C = \Sigma |r(i,j,k) - r(i,j,k+1)|^n$. When n=1, the method is the known minimum-sum-absolute-difference (MSAD) method. When n=2 the method is the very well known but computationally more demanding least-squares method. Any such method, or any of the many known variants and alternatives, may be used according to the invention to generate the displacement array D(i,j,k).

Elasticity Estimation

Once the array of absolute displacement values is determined, the relative local displacement of any given point may be compared with the relative local displacement of points in a surrounding region in order to estimate the elasticity of he tissue in that point. Usually, elasticity at any given point is taken to be the ratio between the displacement of the point and the average local displacement. For example, if as a result of compression, a particular scanned point (represented as its intensity value) was displaced 1 mm axially, and all points around it have also been displaced 1 mm axially, that is, if the relative distance between adjacent points hasn't changed, then it can be assumed that this region did not deform at all and the elasticity at that point is nil. On the other hand, if the distance between the point and its axially adjacent point was initially 0.1 mm but was reduced to 0.09 mm in the next frame, then the relative change will have been 10%, which is proportional to the elasticity.

Figure 2:
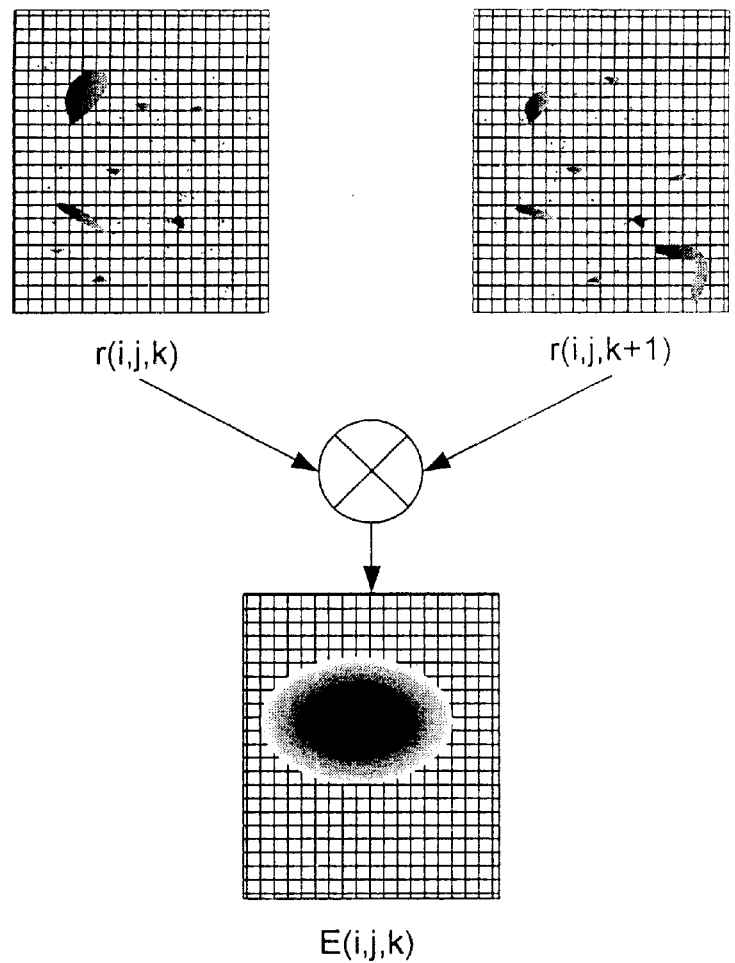
FIG. 2 illustrates how two B-mode (or, equivalently, rf) images are compared to form an elasticity or strain image.

According to the invention, any known method may be used to calculate an elasticity array or "frame" E(i,j,k) given the estimated displacement values D(i,j,k); thus, E(i,j,k)=f (D(i,j,k)), where f is the predetermined function used to convert displacement values to elasticity values. The processing system therefore includes software modules 124, 125 that implement any known algorithms in order to estimate the local displacement values D(i,j,k) and at least one array, that is, "frame" of elasticity (or, equivalently, strain) values E(i,j,k), which are stored in a memory portion 175. The conversion of intensity values r(i,j,k) to the elasticity array E(i,j,k) is illustrated in FIG. 2, which also illustrates how an inclusion (structure) within the interrogation region may be visible in the "E-frame" in the strain or elasticity domain when it is obscured by noise in the original echo intensity domain.

Indexing Convention

In this description, the values for intensity, displacement, and elasticity are said to be represented in "arrays." This terminology is used primarily because it is convenient and intuitive to view an array as a two-dimensional pattern corresponding to the scanned region of interest. Moreover, these values, that is, data sets, will in most cases in fact be stored as arrays within the system because of the ease of indexing and data manipulation this data structure makes possible. Nonetheless, other data structures such as one-dimensional vectors, linked lists, etc., may instead be used to store these values as long as a suitable indexing scheme is adopted to allow for efficient frame registration.

The arrays of intensity, displacement, and elasticity values, all preferably have at least two spatial dimensions (i,j) and the temporal dimension k. Of course, the resolution of the displacement and elasticity calculations, and thus the indices of the arrays D(i,j,k) and E(i,j,k), need not be the same as for the frame data array r(i,j,k). For example, if small regions containing several values of r(i,j,k) and r(i,j,k+1) are averaged, then there will not necessarily be a one-to-one mapping between the arrays r and D, or between D and E. It is assumed here, however, merely by way of example and for the sake of simplicity, that the estimation algorithm compares only two image frames, and that each pixel pair in the two frames generates a single value of the displacement and elasticity arrays D and E. The invention can easily be adapted to accommodate any deviations from these assumptions by using well known array-indexing techniques. Merely by way of example and for the sake of ease of understanding, the spatial indexing of values is assumed below to be the same for all of these arrays, so that, except as needed for clarity, only the time index is indicated for these arrays. Thus, r(k), D(k), and E(k) stand for r(i,j,k), D(i,j,k), and E(i,j,k), respectively.

Moreover, also for the sake of simplicity, only the single time or frame index k is used for E(k) and D(k), even though these arrays are each functions of at least two temporally separated image frames r(i,j,k) and r(i,j,k+1) (or, equivalently, r(i,j,k) and r(i,j,k−1)).

Noise and Artifact Suppression

Ultrasound strain imaging, in general, involves a repetitive process of compression and decompression of the probe (or some other mechanism) on the human body. At the turning points between compression and decompression, the derivative of the displacement will be small, or even zero. Especially at these times, that is, for these frames, strain calculations will be particularly noisy. Moreover, if the operator does not apply a uniform compression/decompression but rather, for example, a twist during the process, then this may also introduce errors into the strain computation. The preferred embodiment of the invention suppresses noise and artifacts through either, and preferably both, of two operations, namely, adaptive persistence and display remapping/colorization.

Adaptive Persistence

Assume that the system has determined that a particular elasticity frame has high reliability. Since approximately the same interrogation region is assumed to be imaged from frame to frame, it would therefore be advantageous to allow the user more time to view this frame. In order to allow this, the preferred embodiment of the invention includes a processing module 127 that implements the adaptive persistence routine described below.

As is well known, persistence of a pixel-based display typically involves some form of weighted average between two pixel arrays. The weighted average may be of actual scanned arrays alone, in which case persistence corresponds approximately to a finite impulse response (FIR) filter, or it may involve recursion, in which case persistence corresponds approximately to an infinite impulse response (IIR) filter; combinations of FIR and IIR techniques also occur.

The preferred persistence algorithm used in the invention is a first-order recursive average of the elasticity frames. For simplicity of notation, let $p(k)_{in}$ be a current pixel in the current strain image frame E(i,j,k) and $p(k)_{out}$ be its value after persistence is applied. $p(k-1)_{in}$ is then the value the pixel had in the previous strain frame E(i,j,k−1). Here, each pixel $p(k)_{in}$ is transformed such that the corresponding output pixel $p(k)_{out}$ is the weighted average of the current input pixel $p(k)_{in}$ and the previous output pixel $p(k-1)_{out}$. Thus, $$(p(k))_{out} = w1 * p(k)_{in} + w2 * p(k-1)_{out} \text{ or, equivalently:}$$

$$(p(k))_{out} = (w1 * p(k)_{in}) / (1 - w2 * z^{-1})$$

where w1 and w2 are weights that determine the degree of persistence decay and $z^{-1}$ is the conventional temporal backward-shift operator. The persisted elasticity array is thus a linear combination of the current, unpersisted elasticity array and at least one previous elasticity array, which is preferably the previous persisted elasticity array. In the preferred embodiment of the invention, the weights are set as follows:

w1=$Q_k$ w2=$(1-Q_k)$ where $Q_k$ is a quality factor.

In the preferred embodiment of the invention, the quality factor $Q_k$ is calculated as a function of either, and preferably both, of two quality metrics, one of which indicates the general noise level of each elasticity frame and the other of which indicates the current displacement change. These metrics are then used to indicate the likely presence of unreliable image frames, whose effect on the displayed information is reduced through adjusting the degree of persistence.

As a first quality metric γ1, which indicates the general noise level in each elasticity frame E(i,j,k), an E-frame averaging module 128 within the processing system 120 calculates the global mean $\mu_k$ of the m*n elements in each elasticity frame E(k). Thus, for each elasticity frame E(k), the scalar value $\mu_k$ is calculated as follows:

$$\mu_k = \frac{1}{m*n}\sum_{i=1}^{m}\sum_{j=1}^{n} E(i, j, k)$$

Of course, $\mu_k$ may also be scaled so as to fall within some desired range.

If $\mu_k$ is relatively low, then the current elasticity frame E(k) likely represents one of two things: 1) large areas of hard, that is, relatively inelastic, tissue; or 2) a pair of image frames during which there was little pressure (displacement changes), such as at a turning point between compression and decompression, or where the user failed to apply the pressure constantly. In either case, the frame probably does not present information with a high SNR. The system may therefore mark as "unreliable" any frame whose value $\mu_k$ is below a predetermined threshold, or may mark it as having varying degrees of likely reliability depending on which of several intervals it falls within, or even where on a continuous scale of reliability it falls.

Figure 4:
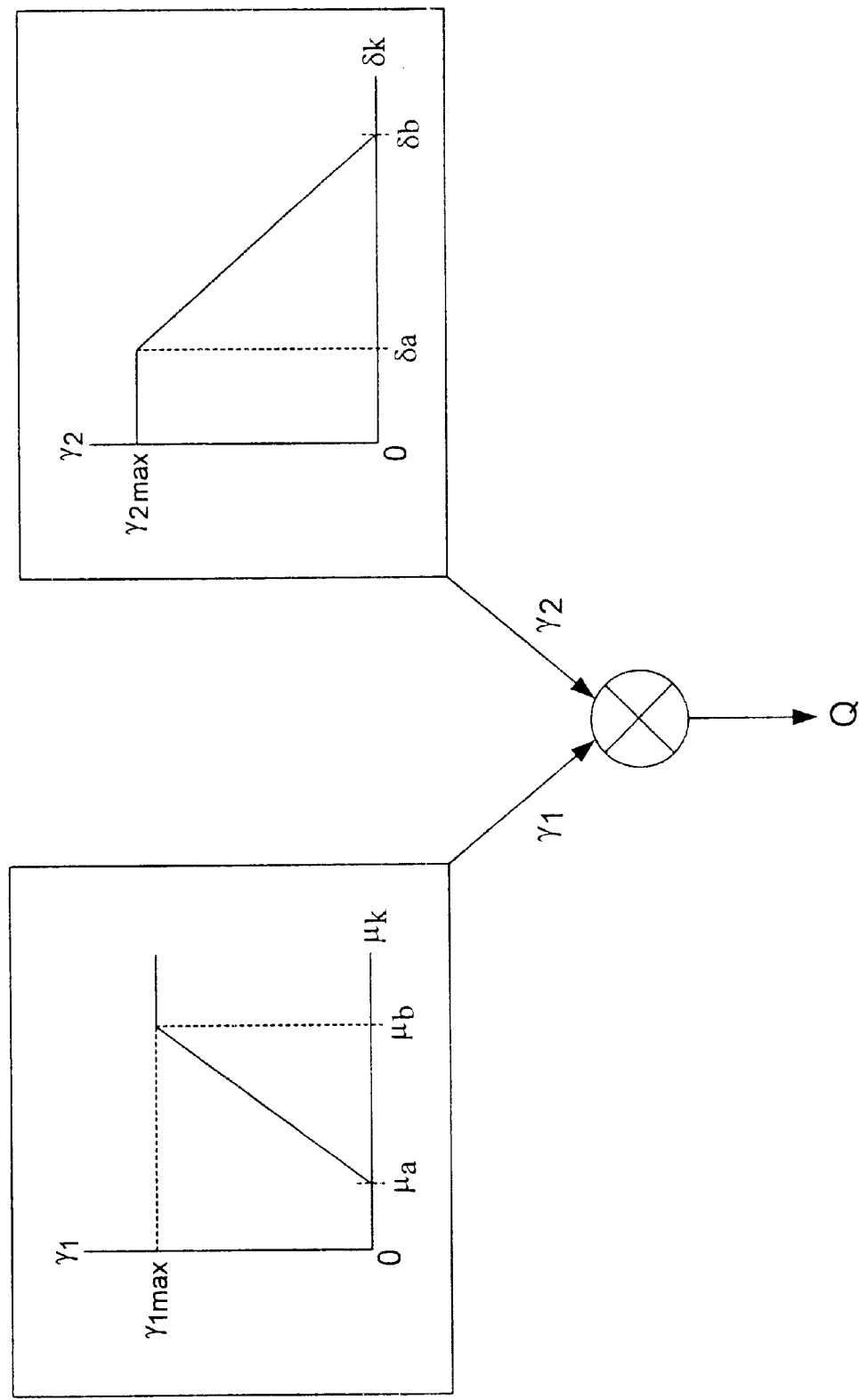
FIG. 4 illustrates the features of different quality metrics that are calculated and combined into a quality factor used to adapt persistence in the preferred embodiment of the invention.

Rather than simply indicating "reliable" or "not reliable," the first quality metric γ1, for each frame, is preferably made a function of $\mu_k$; thus, γ1=γ1($\mu$k). The preferred relationship is illustrated in FIG. 4:

For $\mu_k < \mu_a$, $\quad \gamma_1 = 0$ $\mu_a \leq \mu_k \leq \mu_b$, $\quad \gamma_1 = [\gamma_{1max}/(\mu_b - \mu_a)](\mu_k - \mu_a)$ $\mu_b < \mu_k$, $\quad \gamma_1 = \gamma_{1max}$ The preferred relationship is thus a piece-wise linear function, with $\gamma_1$ rising linearly from zero to a maximum value $\gamma_{1max}$ between breakpoints $\mu_a$ and $\mu_b$. $\gamma_{1max}$, $\mu_a$, and $\mu_b$ may be chosen using normal experimental techniques. One advantage of computing $\gamma_1$ as the illustrated piece-wise linear function is its computational simplicity; indeed, the relationship can be pre-stored in a standard look-up table. It would be possible, however, to calculate $\gamma_1$ using a more complicated function of $\mu_k$. If, for example, $\gamma_1$ were made an exponential function of $\mu_k$, then approximately the same relationship could be expressed using a single breakpoint parameter.

The second quality metric, $\gamma_2$, indicates the current temporal change in displacement for each elasticity frame E(i,j,k). The second quality metric used in the preferred embodiment of the invention is therefore based on a calculation of the mean strain change $\delta_k$ between elasticity frames E(k) and E(k−1). Thus, $\delta_k=\delta_k(\Delta E(k))$, which may be calculated in a processing module 126. Preferably:

$$\delta_k = \frac{1}{m*n}\sum_{i=1}^{m}\sum_{j=1}^{n}|E(i, j, k) - E(i, j, k-1)|$$

As with $\mu_k$, $\delta_k$ may be scaled as desired. Of course, differencing may also be done "forward," such that the intensity frame is compared with the subsequent, rather than the previous frame; this is merely an equivalent change of indexing.

Note that a large value of $\delta_k$ indicates a bad, that is, unreliable strain frame because the change between two successive elasticity frames, should preferably be "smooth," that is, relatively constant. As before, the system may therefore mark as "unreliable" any frame whose $\delta_k$ value is above a predetermined threshold, or may mark it as having varying degrees of likely reliability depending on which of several intervals it falls within, or even where on a continuous scale of reliability it falls. Frames marked as unreliable because of either quality metric may then be suppressed from the ultimate elasticity display.

As with the first quality metric, however, rather than simply indicating "reliable" or "not reliable," the second quality metric $\gamma_2$, for each frame, is preferably made a function of $\delta_k$; thus, $\gamma_2=\gamma_2(\delta_k)$. The preferred relationship is also illustrated in FIG. 4:

For $\delta_k < \delta_a$, $\quad \gamma_2 = \gamma_{2max}$ $\delta_a \leq \delta_k \leq \delta_b$, $\quad \gamma_2 = [\gamma_{2max}/(\delta_a - \delta_b)](\delta_k - \delta_b)$ $\delta_b < \delta_k$, $\quad \gamma_2 = 0$ The preferred relationship for $\gamma_2$ is thus also a piece-wise linear function, with $\gamma_2$ falling linearly from a maximum value $\gamma_{2max}$ to zero between breakpoints $\delta_a$ and $\delta_b$. $\gamma_{2max}$, $\delta_a$, and $\delta_b$ may be chosen using normal experimental techniques. One advantage of computing $\gamma_2$ as the illustrated piece-wise linear function is, as before, its computational simplicity and the relationship can be pre-stored in a standard look-up table. It would be possible, however, to calculate $\gamma_2$ using a more complicated function of $\delta_k$. If, for example, $\gamma_2$ were made an exponential function of $-\delta_k$, then approximately the same relationship could be expressed using a single breakpoint parameter.

The quality factor $Q_k$ is then preferably calculated as a function of both $\gamma_1$ and $\gamma_2$; thus, $Q_k=Q_k(\gamma_1, \gamma_2)$. One possible way to calculate $Q_k$ would be as a linear combination of $\gamma_1$ and $\gamma_2$, with weights chosen using conventional experimental methods. In the preferred embodiment of the invention, however, $Q_k$ is a function of the product of $\gamma_1$ and $\gamma_2$. Thus:

$Q_k=c*\gamma_1*\gamma_2$ where c is an optional scaling constant. Note that $Q_k$ may be calculated and implemented in advance in a look-up table.

One advantage of forming the quality factor as the product of the quality metrics is that if either quality metric $\gamma_1$ or $\gamma_2$ is low, especially zero, then the overall quality factor $Q_k$ will also have a low value, regardless of the value of the other quality metric. Thus, if either $\mu_k<\mu_a$ or $\delta_b<\delta_k$, or, of course, both, then $Q_k=0$.

Now recall the expression for persistence above:

$$p(k)_{out} = w1 * p(k)_{in} - w2 * p(k-1)_{out}$$

$$= Q_k * p(k)_{in} + (1 - Q_k) * p(k-1)_{out}$$

The effect of this persistence is to convert the elasticity frame E(i,j,k) into a persisted elasticity frame $E_p$(i,j,k).

If $\gamma_{1max} = \gamma_{2max} = 1$, then, depending on the chosen breakpoints $\mu_a$, $\mu_b$, $\delta_a$ and $\delta_b$, $Q_k$ will fall in the range [0,1]. If the current elasticity frame has the highest possible quality, then $Q_k = 1$ and the current frame will be displayed without adjustment. If, however, either quality metric indicates an exceptionally bad frame, such that $Q_k = 0$, then the previously displayed frame will continue to be displayed. In order to avoid a single frame being displayed "forever," and so that the user will be able to see deteriorating quality of strain estimation, both $\gamma_{1max}$ and $\gamma_{2max}$ are preferably chosen to be less than unity; some degree of persistence decay will then always be present.

It would be possible to display the persisted elasticity frame as is. In the preferred embodiment of the invention, however, the elasticity frame is first converted into a form suitable for color-coded display; moreover, in the preferred embodiment of the invention, the persisted, color-coded elasticity frame is also overlaid onto a gray-tone display of the original intensity array r(i,j,k), that is, the B-mode image.

Remapping

Figure 3:
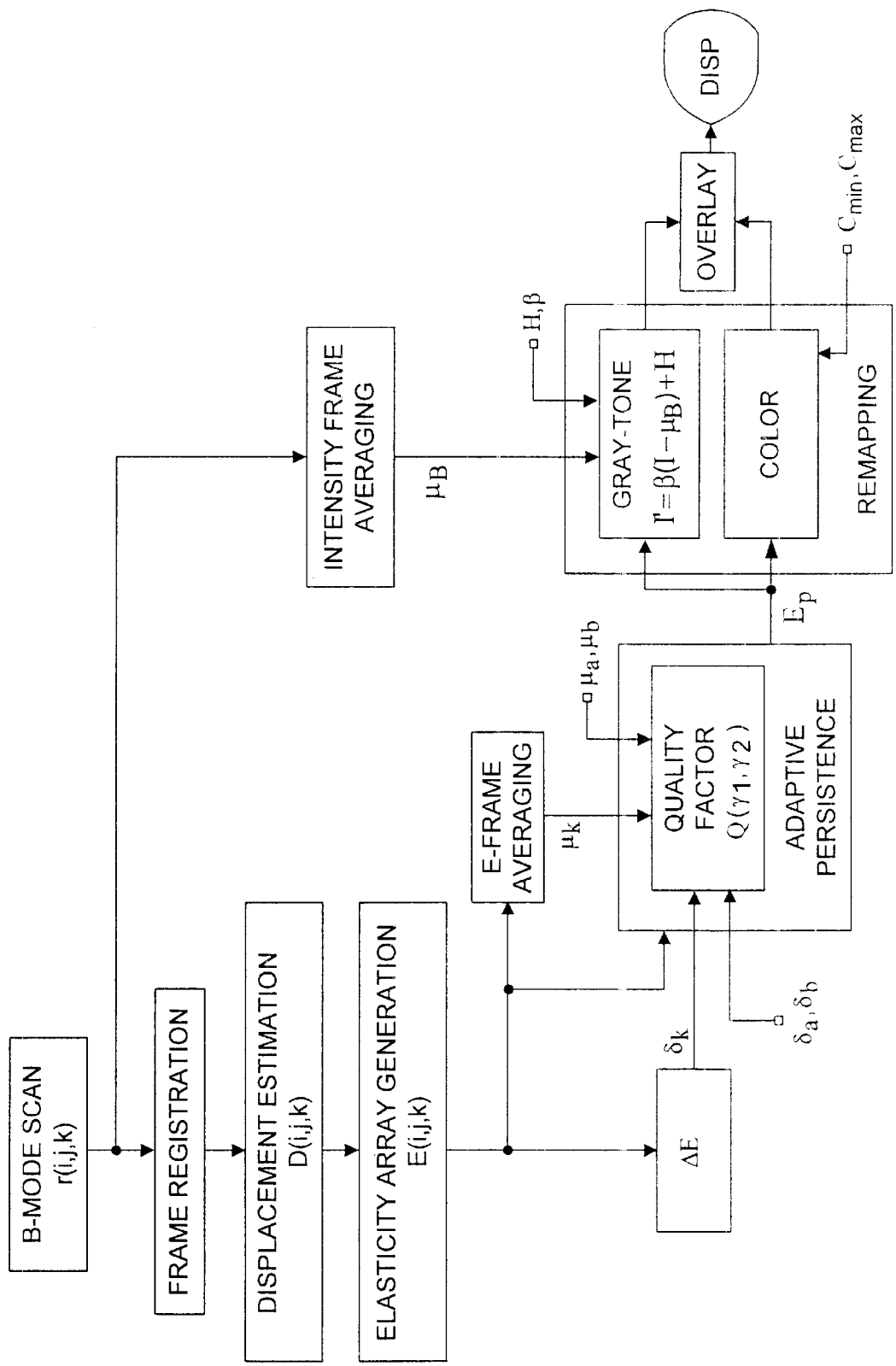
FIG. 3 is a procedural block diagram of the main operations carried out in the preferred embodiment of the invention.

As FIGS. 1 and 3 illustrate, the invention includes a remapping module 129 that remaps the B-mode, that is, echo intensity image into a form most easily interpreted by the user while viewing the display. In the preferred embodiment of the invention, for gray-scale display, the global mean value $\mu_B$ of all the intensity values in the intensity frame is calculated in a processing module 130 is and then used to adjust the gray-scale values of the intensity display. Thus:

$$\mu_B = \frac{1}{m*n} \sum_{i=1}^{m} \sum_{j=1}^{n} r(i, j, k)$$

Using any conventional input method, the user may then adjust a contrast parameter $\beta$ and a brightness parameter H. Alternatively, these values may be predetermined and set, or even adjusted automatically based on any known criteria. These values are then used to generate a remapping table as follows.

Let I=I(i,j,k) be the current intensity (gray-scale) value of each pixel in the current B-mode frame. Each of the pixels in this frame is then remapped to have an intensity I', where:

$$I' = \beta*(I - \mu_p) + H.$$

Once calculated, the remapping table may be stored simply as a look-up table having the same number of values, for example, as there are gray scale values used in the given display. Note that H is the average or base value of intensity that the user wishes to see displayed and that $\beta$ determines how much deviation from the mean value is emphasized in the display. For example, if the intensity value of a pixel is the same as the mean (I=$\mu_p$), then its remapped value will be H. Similarly, if H is set to $\mu_p$ and $\beta=1$, then no pixel's intensity will be changed in the B-mode display. The effect of the remapping is to convert the input B-mode, intensity frame r(i,j,k) into a contrast- and brightness-scaled displayed strain image frame r'(i,j,k), which may then be displayed in the conventional manner.

Color-Coding and Display of Elasticity Data

The invention also preferably provides a method by which the elasticity data is color-coded in order to make it even easier for the diagnostician to detect structures within the interrogation region that have elastic properties different from those of their surroundings. In the preferred embodiment of the invention, color-coding is done by generating a color overlay or transparency that is displayed "on top" of the underlying gray-scale, remapped intensity image.

Because the strain image shows only the tissues with relatively hard or soft responses during an ultrasound exam, there should preferably be some other source of spatial information in order to match the strain values to their corresponding tissues. In a color-overlay embodiment of the invention, the system, in particular, an overlay module 131, combines the remapped intensity image frame r'(i,j,k) with the strain image $E_p$(i,j,k) into a single displayed image. The strain image used in the overlay is preferably the persisted strain frame $E_p$(i,j,k), because it will in general have a higher SNR than the current, non-persisted strain frame. Even a non-persisted strain frame could, however, after colorization, also be used in the overlay.

The overlay module generates a variable color display $I_{overlay}$ by calculating, for each pixel, the following transformation, which is then placed in the buffer typically used by the display driver to generate a display:

$$I_{overlay} = (1-\alpha)*I_{gray} + \alpha a * C[E_p(r,g,b)],$$

where $I_{gray}$=r(i,j,k) is the value of the intensity in the original gray scale tissue image (B-mode), C is a color map that maps the persisted strain image $E_p$ to a color-coded version, and $\alpha$ is a transmission coefficient between 0 and 1. Obviously, if $\alpha=1$, then only a color map of the elasticity values will be displayed; for $\alpha=0$, the B-mode display will be seen as if no elasticity calculations were done at all. The value a is preferably adjustable by the viewer using any conventional input device; alternatively, a may be set to some experimentally predetermined value.

Figure 5:
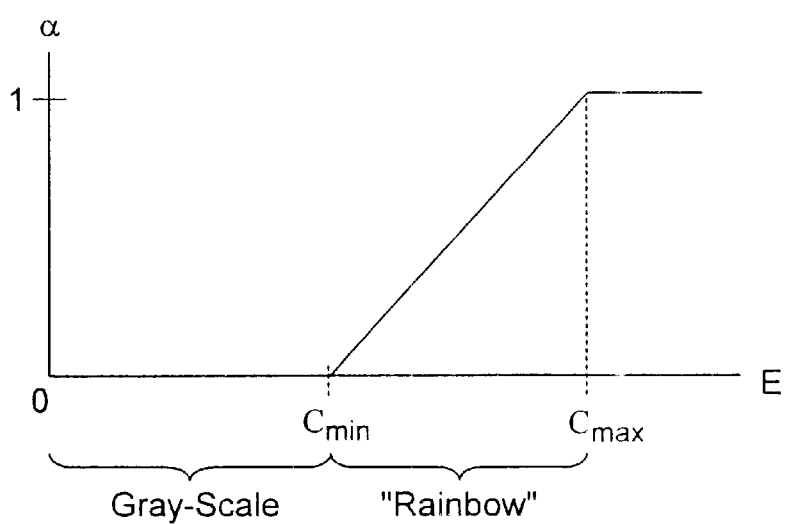
FIG. 5 illustrates a preferred color-mapping relationship used in the preferred embodiment of the invention.

FIG. 5 illustrates the general principle of color-coding used in the preferred embodiment of the invention: Depending on the strain value, the colorization parameter a remains equal to zero in a "Gray-Scale" range when the elasticity value is less than a value $C_{min}$ and then rises linearly over a "Rainbow" range as the elasticity value increases from $C_{min}$ to $C_{max}$, and then remains at a maximum when the elasticity value is greater than $C_{max}$. $C_{min}$ and $C_{max}$ may be determined using normal experimental methods and may also be made user-adjustable. Note that the lower $C_{min}$ is chosen to be, the sooner color will appear in the display: Adjusting $C_{min}$ and $C_{max}$ changes the range of sensitivity or "color contrast" of the display.

According to the expression above for $I_{overlay}$, the overlaid display is generated as a linear combination of the gray-scale image and the color-coded elasticity image. One advantage of using such a linear combination is that it is relatively fast to compute. As faster processors become available, however, even non-linear combinations could be used to generate $I_{overlay}$ and that might enhance the quality of the display. For example, the product of the gray scale and elasticity color frames (possibly scaled as needed using a set or adjustable constant) might enhance or suppress the color presentation of highly reflective tissue. Even other non-linear combinations or weighting coefficients could be used, depending on known or assumed properties of the tissue to be imaged and the degree to which either the gray-scale or color-coded elasticity image is to be emphasized in different conditions.

The expression above may be used as is for real-time color-coding of the strain display. A more easily interpreted combined elasticity/B-mode image may be generated in cine mode, however, by operating on an entire stored sequence of B-mode and strain image frames.

In order to maintain a consistent representation of elasticity in frame-to-frame presentation in cine mode, the strain image $E_p(i,j,k)$ used for colorization is preferably first normalized and adjusted to bring out differing degrees of elasticity in the acquired frames. In the preferred embodiment of the invention, a standard histogram equalization method is therefore applied to each persisted strain image so that a fixed color table can be used to represent the elasticity of tissue. This method is well known, but can be summarized as follows: As in B-mode, the intensity values in the elasticity or strain frame $E_p(i,j,k)$ will typically fall in a range from 0 to, for example, 255, depending obviously on the type of display screen used.

It would be impractical and confusing, however, to display as many as 256 different colors. Instead, the 256 (for example) possible values are grouped into a smaller number, for example, 16, of intervals or "bins." Each pixel whose value falls in a particular range is therefore counted in the corresponding bin. When all strain values are counted in their appropriate bins, the resulting histogram will indicate the distribution of elasticity values but with a smaller number of groups rather than a potentially large number of discrete values.

In one prototype of the invention, the bins were assigned colors according to a scale that approximates the relationship shown in FIG. 5. Each pixel having a value falling in, say, bin (interval) number 4, would be rendered using the color assigned to bin 4. The colors preferably range from blue to red, with either "extreme" color used to indicate maximum hardness (lowest strain value) and the other used to indicate maximum softness (highest strain value).

On-Screen Image Quality Guide

Figure 6:
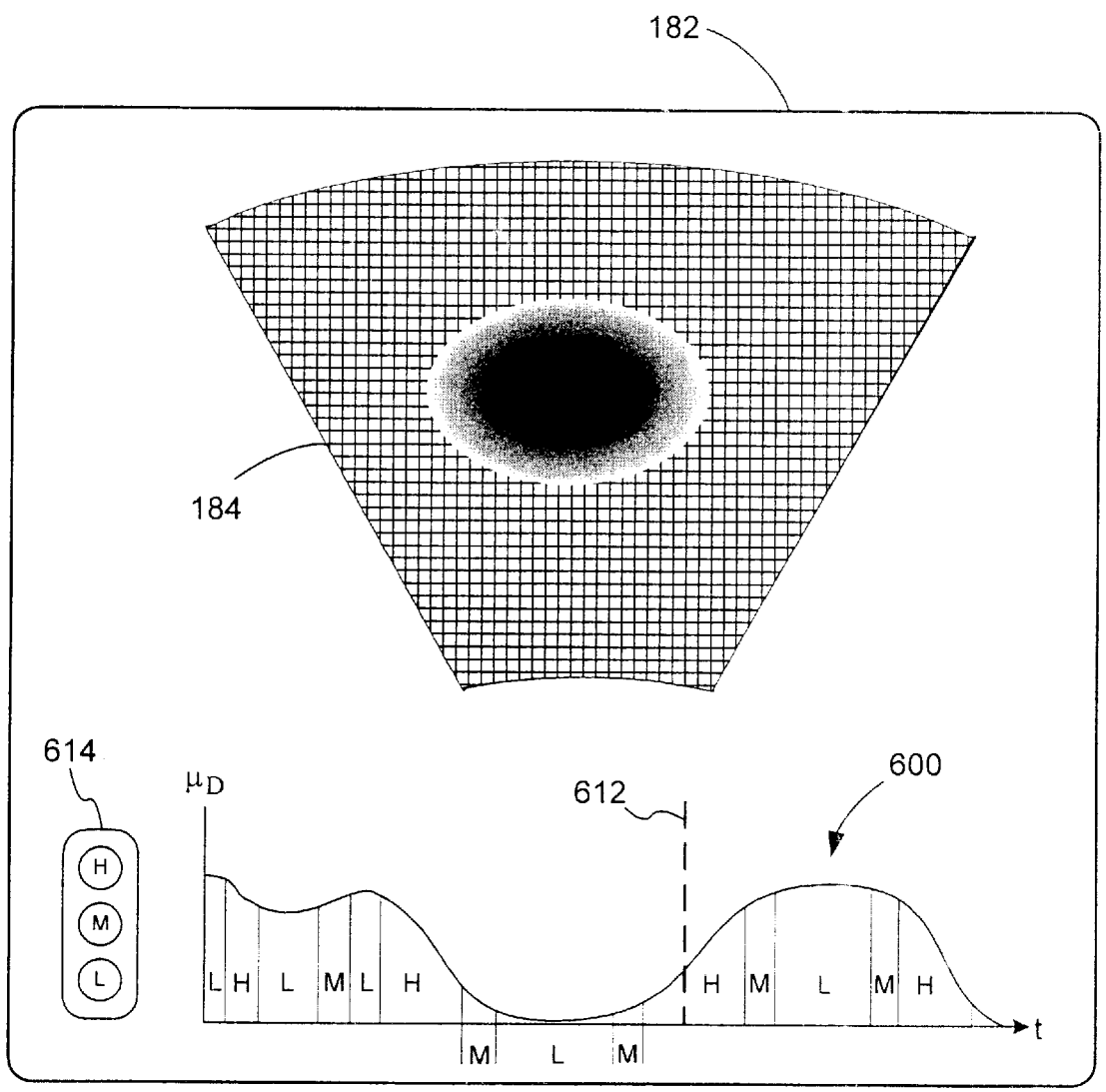
FIG. 6 illustrates a probe motion guide and image quality indicator that acts not only as a frame quality indicator, but also, in some cases, as an aide to the user in maneuvering the ultrasound probe.

The invention preferably also includes a software module 132 within the processing system, which may be implemented using known programming techniques and which calculates the parameters and display characteristics of a frame quality guide 600. FIG. 6 illustrates a hypothetical strain image display 184 in which an example of such a frame quality guide 600 is included. In this example, the guide is a plot of the current mean frame-to-frame displacement JAD as a function of time (or, equivalently, frame number). For example:

$$\mu_D = \frac{1}{m*n} \sum_{i=1}^{m} \sum_{j=1}^{n} D(i,j,k)$$

In the illustrated plot, the average displacement is shown as being roughly sinusoidal, which is the preferred profile that the user should follow when generating compression and decompression with the probe against the patient's body.

In order to identify which frame is currently being displayed, and what its corresponding guide parameter (such as $\mu_D$) is, a marker 612 such as a line is preferably included within the displayed guide 610. In the illustrated guide, different portions of the displacement plot are labeled as "H", "M" and "L" to indicate that they correspond to frames with relatively high, medium or low reliability, determined using any of the metrics described above, such as the quality factor $Q_k$.

Recall that the best SNR will usually be where the change in displacement (average velocity) is highest. The measure of reliability may therefore also be an estimate of the change in mean displacement (proportional to $d\mu_D/dk$) from frame-to-frame, or over more than two frames. The indicators "H", "M" and "L" may then be chosen to correspond to different intervals of the change estimates.

There are several ways in which this may be indicated to the user. Any portion of the plot where the reliability is high, medium and low may, for example, be shown in green, yellow and red, respectively. Alternatively, some other graphical device such as a green-yellow-red (corresponding to high, medium and low reliability, respectively) "traffic light" quality indicator 614, or a single display field that changes color between green, yellow and red, may instead be included to indicate the level of frame quality for the currently displayed frame. Yet another indicator, which allows for more than three quality classifications, would be a segmented indicator such as is found on many volume controls—the higher the quality, the more segments are illuminated, with the higher ones being green, for example.

Using any conventional input device, such as simply moving the marker 612, for example, by holding positioning an on-screen (or turning a knob, etc.) cursor on the marker, holding down a mouse button or similar device, and "dragging" the marker 612 to a frame of interest, or by maneuvering a dial or knob, the user may select different frames for display, whereby the actual display system 180 is caused, using conventional techniques, to update the current display 184 accordingly. Alternatively, the user may select a frame for display in any conventional manner, and the system will then position the marker 612 accordingly so as to indicate the quality of the selected frame.

Note that the mean frame-to-frame displacement $\mu_D$ is not the only parameter that can be used as the basis for the guide 600. For example, the quality factor Q could be used instead. Moreover, as long as some measure of image quality in some chosen sense is calculated the guide 610 could also be implemented in other display systems operating in cine mode, which allow frame-by-frame viewing of images, even systems that generate only B-mode images.

The invention may also generate more than one marker 612. For example, if the invention generates two on-screen markers, then the user could move these, again, for example, by dragging them with a displayed cursor, so as to bracket a section of the plot, for example, a section shown as having high reliability. Only these frames may then be displayed repeatedly in a cine loop, thereby eliminating sections corresponding to elasticity frames of lower reliability.

In FIG. 6, note that there is a "dip" in the leftmost "peak." This is to illustrate how the user might fail to follow the preferred compression profile. Conventional elasticity displays would show the corresponding frames just as any other, although these frames will have a low SNR and will be distracting.

The embodiment illustrated in FIG. 6 will be most useful in cine mode, that is, where there are many frames stored for later analysis. It would also be possible to include the quality indicator 614 in the real-time elasticity display, although the indicator would usually change too fast to be useful, except perhaps as a training aide, and might itself be a significant distraction.

What is claimed is:

1. An ultrasonic imaging method comprising the following steps:

repeatedly scanning a region of interest (ROI) of a body with an ultrasound transducer and thereby acquiring a first and a second set of intensity values, each intensity value representing an imaging property of a respective portion of the ROI;

generating a gray-scale representation of the first set of intensity values;

calculating an elasticity data set of elasticity values as a function of differences between corresponding intensity values in the first and second sets of intensity values;

generating a color representation of the elasticity data set by color-coding the elasticity values;

simultaneously displaying the gray-scale representation and the color representation as a single, overlaid display.

2. A method as in claim 1, further comprising the following steps:

generating the overlaid display as a linear combination of the gray-scale representation and the color representation; and adjusting a display visibility of the gray-scale representation and the color representation, respectively, as a first and second function of a transmission coefficient.

3. A method as in claim 2, in which the transmission coefficient is user-adjustable.

4. A method as in claim 2, in which the step of generating the overlaid display comprises computing the linear combination according to:

$$I_{overlay}=(1-\alpha)*I_{gray}+\alpha*C[E]$$

where:

$I_{overlay}$ is the overlaid display;

$I_{gray}$ is the gray-scale representation;

$C[E]$ is the color representation; and $\alpha$ is the transmission coefficient.

5. A method as in claim 1, further comprising the step of generating the overlaid display as a non-linear combination of the gray-scale representation and the color representation.

6. A method as in claim 1, further comprising the following steps:

adaptively persisting the elasticity data set, repeating the step of calculating the elasticity data set for a plurality scans of the ROI and, for each scan, generating a corresponding one of the elasticity data sets; and for at least a current one of the elasticity data sets, calculating a quality factor; in which:

the step of generating the color representation comprises color-coding the elasticity values in the persisted elasticity data set; and the step of adaptively persisting the elasticity data set includes generating a persisted elasticity frame as a persistence function that has, as arguments, the current elasticity data set, the quality factor, and at least one earlier generated elasticity data set.

7. A method as in claim 1, further comprising:

calculating a quality value that indicates an estimated measure of quality of the elasticity data set;

displaying a graphical representation of the quality value along with the overlaid display.

8. An ultrasonic imaging system comprising:

an ultrasound transducer;

control means for controlling transmission and reception of ultrasound by the transducer and thereby for controlling repeated scanning of a region of interest (ROI) of a body with ultrasound generated by the transducer and for acquiring a first and a second set of intensity values, each intensity value representing an imaging property of a respective portion of the ROI;

a processing system including:

means for generating a gray-scale representation of the first set of intensity values;

elasticity estimation means for calculating an elasticity data set of elasticity values as a function of differences between corresponding intensity values in the first and second sets of intensity values;

remapping means of generating a color representation of the elasticity data set by color-coding the elasticity values; and overlay generation means for generating a single, overlaid display of the gray-scale representation and the color representation; and display means for displaying the single, overlaid display.

9. A system as in claim 8, in which the overlay generation means is provided for generating the overlaid display as a linear combination of the gray-scale representation and the color representation;

further including means for adjusting a display visibility of the gray-scale representation and the color representation, respectively, as a first and second function of a transmission coefficient.

10. A system as in claim 9, in which the means for adjusting the display visibility is user-adjustable.

11. A system as in claim 8, further comprising persistence means:

for adaptively persisting the elasticity data set before the remapping means generates the color representation of the elasticity data set by color-coding, and for calculating a quality factor of the elasticity data set and for adaptively persisting the elasticity data set as a persistence function that has, as arguments, the elasticity data set itself, the quality factor, and at least one earlier generated elasticity data set.

12. A system as in claim 8, further comprising guide generation means for generating a graphical representation of a quality value along with the overlaid display, the quality value indicating an estimated measure of quality of the elasticity data set.

13. An ultrasonic imaging method comprising the following steps:

repeatedly scanning a region of interest (ROI) of a body with an ultrasound transducer and acquiring first and second data sets of echo values, each echo value representing an imaging property of a respective portion of the ROI;

calculating an elasticity data set of elasticity values as a function of differences between corresponding echo values in the first and second data sets;

generating a display of the elasticity data set;

adaptively persisting the generated display;

repeating the step of calculating the elasticity data set for a plurality scans of the ROI and, for each scan, generating a corresponding one of the elasticity data sets; and for at least a current one of the elasticity data sets, calculating a quality factor;

in which:

the step of adaptively persisting the display includes generating a persisted elasticity frame as a persistence function that has, as arguments, the current elasticity data set, the quality factor, and at least one earlier generated elasticity data set; and the step of generating the display comprises displaying a representation of the persisted elasticity frame.

14. A method as in claim 13, further comprising generating the persisted elasticity frame as a linear combination of the current elasticity data set and at least one previous elasticity data set.

15. A method as in claim 14, in which the previous elasticity data set is an immediately preceding persisted elasticity data set.

16. A method as in claim 14, in which the linear combination is a sum of a first term and a second term, in which:
the first term is the product of the current elasticity data set and a quality factor;
the second term is the product of the preceding persisted elasticity data set and a function of the quality factor that decreases as the quality factor increases.

17. A method as in claim 13, which the step of calculating the quality factor comprises calculating a quality metric as a function of a mean value of the plurality of elasticity values in the current elasticity frame.

18. A method as in claim 17, in which the function of the mean value of the plurality of elasticity values increases from a minimum to a maximum metric value as the means value increases.

19. A method as in claim 17, in which the step of calculating the quality factor comprises calculating a quality metric as a function of a measure of change between the current elasticity data set and a preceding elasticity data set.

20. A method as in claim 19, in which the function of the measure of change decreases from a maximum to a minimum metric value as the measure of change increases.

21. An ultrasonic imaging system comprising:
an ultrasound transducer;
control means for controlling transmission and reception of ultrasound by the transducer and thereby for controlling repeated scanning of a region of interest (ROI) of a body with ultrasound generated by the transducer, and for acquiring a first and a second set of intensity values, each intensity value representing an imaging property of a respective portion of the ROI;
a processing system including:
elasticity estimation means for calculating an elasticity data set of elasticity values as a function of differences between corresponding intensity values in the first and second sets of intensity values;
persistence means:
for adaptively persisting the generated display;
for calculating a quality factor for at least a current one of the elasticity data sets; and
for generating a persisted elasticity frame as a persistence function that has, as arguments, the current elasticity data set, the quality factor, and at least one earlier generated elasticity data set;
display means for displaying a representation of the persisted elasticity frame.

22. A system as in claim 21, in which the persistence means is provided for calculating a mean value of the plurality of elasticity values in the current elasticity frame and for calculating the quality factor as a function of the mean value.

23. A system as in claim 21, in which the persistence means is provided for calculating a measure of change between the current elasticity data set and a preceding elasticity data set and for calculating the quality factor as a function of the measure of change.

24. An ultrasonic imaging method comprising:
repeatedly scanning a region of interest (ROI) of a body with an ultrasound transducer and thereby acquiring a plurality of intensity data sets of intensity values, each intensity value representing an imaging property of a respective portion of the ROI;
for each of at least one pair of the intensity data sets, calculating a corresponding displacement data set having displacement elements, each displacement element quantifying displacement of a respective ROI portion over a time interval between the respective pair of intensity data sets;
for each displacement data set, calculating a display data set as a function of the displacement elements in the respective displacement data set;
selecting one of the display data sets for display; and
displaying both the selected display data set and a graphical representation of a quality value that indicates an estimated measure of quality of the selected display data set.

25. A method as in claim 24, further comprising:
for each display data set, calculating a guide parameter; and
displaying a graphical representation of the guide parameter along with the selected display data set and graphical representation of the current quality value.

26. A method as in claim 25, in which the guide parameter is calculated as a mean value of the displacement elements in the displacement data set corresponding to the display data set.

27. A method as in claim 26, in which the quality value is calculated as a function of the change of the mean values of the displacement elements in displacement data sets corresponding to a plurality of sequential scans.

28. A method as in claim 25, further comprising:
calculating the guide parameter and quality value for each display data set; and
displaying a composite display guide that comprises a composite graphical representation of the guide parameters and corresponding quality values.

29. A method as in claim 24, further including the following steps:
for each displacement data set, calculating an elasticity data set as a function of the displacement data set; and
calculating each display data set as a function of the calculated elasticity data set corresponding to the respective displacement data set.

30. An ultrasonic imaging system comprising:
an ultrasound transducer;
control means for controlling transmission and reception of ultrasound by the transducer and thereby for controlling repeated scanning of a region of interest (ROI) of a body with ultrasound generated by the transducer, and for acquiring a first and a second set of intensity values, each intensity value representing an imaging property of a respective portion of the ROI;
a processing system including:
displacement estimation means for calculating, for each of at least one pair of the intensity data sets, a corresponding displacement data set having displacement elements, each displacement element quantifying displacement of a respective ROI portion over a time interval between the respective pair of intensity data sets, and, for each displacement data set, for calculating a display data set as a function of the displacement elements in the respective displacement data set;
guide generation means for generating a graphical representation of a quality value, the quality value indicating an estimated measure of quality of the elasticity data set; and display means for displaying both a selected display data set and the graphical representation of the corresponding quality value.

31. A system as in claim 30, in which:

the guide generation means is further provided for calculating a respective guide parameter for each display data set; and the display means is further provided for displaying a representation of the guide parameter along with the selected display data set and the graphical representation of the current quality value.

32. A system as in claim 31, further comprising frame selection means for presenting to a user a displayed indicator of the guide parameter, for sensing user selection of one of the display data sets for display, and for directing the display means to display the selected display data set.

* * * * *

UNITED STATES PATENT AND TRADEMARK OFFICE
CERTIFICATE OF CORRECTION

PATENT NO.     : 6,558,324 B1
DATED          : May 6, 2003
INVENTOR(S)    : Patrick L. Von Behren et al.

It is certified that error appears in the above-identified patent and that said Letters Patent is hereby corrected as shown below:

<u>Title page,</u>
Item [75], Inventors, delete "Dong-Cyuan Liu" and substitute -- Dong Chyuan Liu -- in its place.

Signed and Sealed this

Ninth Day of September, 2003

JAMES E. ROGAN
*Director of the United States Patent and Trademark Office*